(12) United States Patent
Dos Santos et al.

(10) Patent No.: US 9,782,541 B2
(45) Date of Patent: Oct. 10, 2017

(54) TEMPERATURE CONTROL DEVICE AND THERMAL SENSOR ASSEMBLY FOR MEDICAL DEVICE

(75) Inventors: Cesario Dos Santos, Aliso Viejo, CA (US); Robert J. Sanchez, Jr., Oceanside, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 1182 days.

(21) Appl. No.: 12/444,000

(22) PCT Filed: Oct. 1, 2007

(86) PCT No.: PCT/US2007/080078
§ 371 (c)(1),
(2), (4) Date: Apr. 2, 2009

(87) PCT Pub. No.: WO2008/108886
PCT Pub. Date: Sep. 12, 2008

(65) Prior Publication Data
US 2010/0106089 A1    Apr. 29, 2010

Related U.S. Application Data

(60) Provisional application No. 60/921,497, filed on Oct. 16, 2006, provisional application No. 60/921,499, (Continued)

(51) Int. Cl.
*A61M 5/145* (2006.01)
*A61M 5/142* (2006.01)
(Continued)

(52) U.S. Cl.
CPC ............ *A61M 5/20* (2013.01); *A61F 9/0017* (2013.01); *A61M 5/14244* (2013.01);
(Continued)

(58) Field of Classification Search
USPC ...... 604/114, 20–26, 28, 31, 294, 181, 6.13, 604/291; 165/46; 433/32; 392/304, 311,
(Continued)

(56) References Cited

U.S. PATENT DOCUMENTS 1,252,614 A     1/1918   Pieper
2,491,266 A  * 12/1949   Hooper ................... 392/459
(Continued)

FOREIGN PATENT DOCUMENTS

AU     7623298     6/1998
CA     1313802     2/1993
(Continued)

OTHER PUBLICATIONS

Ultra™ 2800 Positive Displacement; 2004; EFD, Inc. Brochure XP 1104 vol. 11.10; 2 pages.
(Continued)

*Primary Examiner* — Nathan R Price
*Assistant Examiner* — Weng Lee
(74) *Attorney, Agent, or Firm* — Kenneth D. Bassinger

(57) ABSTRACT

A dispensing assembly has a dispensing chamber housing, a temperature control device, a thermal sensor, and an interface. The dispensing chamber housing has an inner surface, an outer surface, and a wall thickness. The inner surface partially defines a dispensing chamber for receiving a quantity of a substance. The temperature control device at least partially surrounds the dispensing chamber housing. The temperature control device alters a temperature of a substance in the dispensing chamber. The temperature control device and the thermal sensor are located on a substrate. The substrate is wrapped around an exterior surface of the dispensing chamber housing. The interface is connected to the temperature control device and the thermal sensor. An interface connector is connected to the interface. The dis-
(Continued)

tance between the temperature control device and the thermal sensor is approximately equal to the wall thickness of the dispensing chamber housing.

19 Claims, 5 Drawing Sheets

Related U.S. Application Data filed on Oct. 16, 2006, provisional application No. 60/921,498, filed on Oct. 16, 2006.

(51) Int. Cl.
| | | |
|---|---|---|
| *A61M 5/20* | (2006.01) | |
| *A61F 9/00* | (2006.01) | |
| *A61M 5/31* | (2006.01) | |
| *A61M 5/44* | (2006.01) | |
| *A61M 5/315* | (2006.01) | |
| *A61M 5/14* | (2006.01) | |

(52) U.S. Cl.
CPC .... *A61M 5/14526* (2013.01); *A61M 5/14546* (2013.01); *A61M 5/14566* (2013.01); *A61M 5/3129* (2013.01); *A61M 5/445* (2013.01); *A61M 5/1413* (2013.01); *A61M 5/31511* (2013.01); *A61M 2005/14268* (2013.01); *A61M 2205/3368* (2013.01); *A61M 2205/3653* (2013.01); *A61M 2205/50* (2013.01); *A61M 2205/6027* (2013.01); *A61M 2205/8206* (2013.01); *A61M 2210/0612* (2013.01)

(58) Field of Classification Search
USPC .......................................................... 392/314
See application file for complete search history.

(56) References Cited

U.S. PATENT DOCUMENTS

| | | | | |
|---|---|---|---|---|
| 2,710,909 | A | * | 6/1955 | Logan et al. ................ 338/212 |
| 3,089,815 | A | | 5/1963 | Lieb et al. |
| 3,199,740 | A | | 8/1965 | Huffa et al. |
| 3,608,549 | A | | 9/1971 | Merrill |
| 3,858,581 | A | | 1/1975 | Kamen |
| 3,892,537 | A | | 7/1975 | Gulati et al. |
| 3,982,537 | A | | 9/1976 | Bucalo |
| 4,007,742 | A | | 2/1977 | Banko |
| 4,030,499 | A | | 6/1977 | Bucalo |
| 4,054,138 | A | | 10/1977 | Bucalo |
| 4,122,850 | A | | 10/1978 | Bucalo |
| 4,184,510 | A | | 1/1980 | Murry et al. |
| 4,246,932 | A | | 1/1981 | Raines |
| 4,265,618 | A | | 5/1981 | Herskovitz et al. |
| 4,357,136 | A | | 11/1982 | Herskovitz et al. |
| 4,392,827 | A | | 7/1983 | Martin |
| 4,474,752 | A | | 10/1984 | Haslam et al. |
| 4,484,915 | A | | 11/1984 | Tartaglia |
| 4,582,488 | A | | 4/1986 | Newman |
| 4,684,344 | A | | 8/1987 | Brockway et al. |
| 4,704,088 | A | | 11/1987 | Newman |
| 4,713,446 | A | | 12/1987 | DeVore et al. |
| 4,764,165 | A | | 8/1988 | Reimels et al. |
| 4,795,423 | A | | 1/1989 | Osterholm |
| 4,810,859 | A | * | 3/1989 | Anabtawi et al. ............ 219/535 |
| 4,830,855 | A | | 5/1989 | Stewart |
| 4,911,161 | A | | 3/1990 | Schechter |
| 4,992,045 | A | | 2/1991 | Beisel |
| 5,066,276 | A | | 11/1991 | Wang |
| 5,120,307 | A | | 6/1992 | Wang |
| 5,271,085 | A | * | 12/1993 | Carballo ..................... 392/444 |
| 5,328,481 | A | | 7/1994 | Wang |
| 5,336,175 | A | | 8/1994 | Mames |
| 5,360,413 | A | | 11/1994 | Leason et al. |
| 5,370,630 | A | | 12/1994 | Smidebush et al. |
| 5,431,630 | A | | 7/1995 | Leonard |
| 5,476,511 | A | | 12/1995 | Gwon et al. |
| 5,487,725 | A | | 1/1996 | Peyman |
| 5,503,144 | A | | 4/1996 | Bacon |
| 5,582,595 | A | | 12/1996 | Haber et al. |
| 5,602,188 | A | | 2/1997 | Nakanishi |
| 5,620,700 | A | | 4/1997 | Berggren et al. |
| 5,662,612 | A | | 9/1997 | Niehoff |
| 5,743,886 | A | | 4/1998 | Lynn et al. |
| 5,773,019 | A | | 6/1998 | Ashton et al. |
| 5,783,205 | A | | 7/1998 | Berggren et al. |
| 5,824,072 | A | | 10/1998 | Wong |
| 5,860,949 | A | | 1/1999 | Chen |
| 5,882,338 | A | | 3/1999 | Gray |
| 5,928,197 | A | | 7/1999 | Niehoff |
| 5,928,663 | A | | 7/1999 | Peyman |
| 5,984,889 | A | | 11/1999 | Christ et al. |
| 5,989,238 | A | * | 11/1999 | Ginsburg ..................... 604/500 |
| 6,051,011 | A | | 4/2000 | Weidenbenner |
| 6,165,190 | A | | 12/2000 | Nguyen |
| 6,210,357 | B1 | | 4/2001 | Morris |
| 6,221,045 | B1 | | 4/2001 | Duchon et al. |
| 6,259,074 | B1 | * | 7/2001 | Brunner et al. ............. 219/497 |
| 6,270,343 | B1 | | 8/2001 | Martin |
| 6,290,690 | B1 | | 9/2001 | Huculak et al. |
| 6,311,868 | B1 | | 11/2001 | Krietemeier et al. |
| 6,364,865 | B1 | | 4/2002 | Lavi et al. |
| 6,372,245 | B1 | | 4/2002 | Bowman et al. |
| 6,372,246 | B1 | | 4/2002 | Bowman et al. |
| 6,413,245 | B1 | | 7/2002 | Yaacobi et al. |
| 6,419,656 | B1 | | 7/2002 | Vetter et al. |
| 6,436,143 | B1 | | 8/2002 | Ross et al. |
| 6,488,659 | B1 | | 12/2002 | Rosenman |
| 6,520,930 | B2 | | 2/2003 | Critchlow et al. |
| 6,585,700 | B1 | | 7/2003 | Trocki et al. |
| 6,595,979 | B1 | | 7/2003 | Epstein et al. |
| 6,620,189 | B1 | | 9/2003 | Machoold et al. |
| 6,635,267 | B1 | | 10/2003 | Miyoshi et al. |
| 6,645,179 | B1 | | 11/2003 | Ishikawa et al. |
| 6,726,654 | B2 | | 4/2004 | Rosenman |
| 6,940,209 | B2 | | 9/2005 | Henderson |
| 6,991,457 | B2 | | 1/2006 | Kazen et al. |
| 7,176,030 | B2 | | 2/2007 | Faries, Jr. et al. |
| 2002/0055720 | A1 | | 5/2002 | Hohlfelder et al. |
| 2003/0055380 | A1 | | 3/2003 | Flaherty |
| 2003/0125665 | A1 | | 7/2003 | Rosenman |
| 2004/0039253 | A1 | | 2/2004 | Peyman et al. |
| 2004/0052761 | A1 | | 3/2004 | Vernon et al. |
| 2004/0054319 | A1 | | 3/2004 | Langley et al. |
| 2004/0133155 | A1 | | 7/2004 | Varner et al. |
| 2004/0167466 | A1 | | 8/2004 | Drasler et al. |
| 2004/0176720 | A1 | | 9/2004 | Kipfer |
| 2004/0204673 | A1 | | 10/2004 | Faherty |
| 2004/0210200 | A1 | | 10/2004 | Gerondale et al. |
| 2004/0231667 | A1 | | 11/2004 | Horton et al. |
| 2005/0065477 | A1 | | 3/2005 | Jost |
| 2006/0047250 | A1 | | 3/2006 | Hickingbotham |
| 2007/0016186 | A1 | | 1/2007 | LoRusso |
| 2007/0060887 | A1 | | 3/2007 | Marsh et al. |
| 2007/0142769 | A1 | | 6/2007 | Griffiths et al. |
| 2007/0270750 | A1 | | 11/2007 | Dacquay et al. |
| 2009/0069806 | A1 | | 3/2009 | De La Mora Levy et al. |

FOREIGN PATENT DOCUMENTS

| | | |
|---|---|---|
| DE | 3434930 A1 | 4/1986 |
| EP | 0 516 292 | 2/1922 |
| EP | 0348146 A1 | 6/1989 |
| EP | 0356372 A2 | 2/1990 |
| EP | 0398394 | 11/1990 |
| EP | 0520443 A2 | 12/1992 |
| EP | 1516638 | 3/2005 |
| EP | 1704840 A1 | 9/2006 |
| GB | 1551767 | 5/1979 |
| JP | 2002/059055 A | 2/2002 |
| RU | 2270032 C2 | 2/2006 |
| SU | 285170 | 10/1970 |
| WO | WO 82/03761 | 11/1982 |

(56) References Cited

FOREIGN PATENT DOCUMENTS

| | | |
|---|---|---|
| WO | WO 87/00029 | 1/1987 |
| WO | WO 93/11818 | 6/1993 |
| WO | WO 96/03978 | 2/1996 |
| WO | WO 99/33853 | 7/1999 |
| WO | WO 00/74752 A1 | 12/2000 |
| WO | WO 01/10482 A1 | 2/2001 |
| WO | WO 02/07658 A1 | 1/2002 |
| WO | WO 03/006098 | 1/2003 |
| WO | WO 2005/027578 A1 | 3/2005 |
| WO | WO 2006/037969 | 4/2006 |
| WO | WO 2006/050008 A1 | 5/2006 |
| WO | WO 2006/067480 | 6/2006 |
| WO | WO 2006/108026 A2 | 10/2006 |

OTHER PUBLICATIONS

Parker: Your Resource for Motion and Fluid Control Components, Systems and Solutions—Systems Solutions for Life Sciences; 2003; Aurora Instruments, LLC Brochure; 8 pages.

* cited by examiner

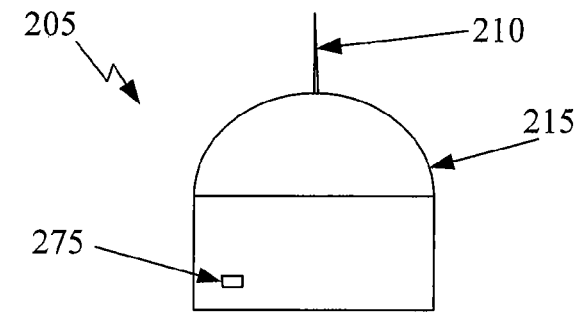
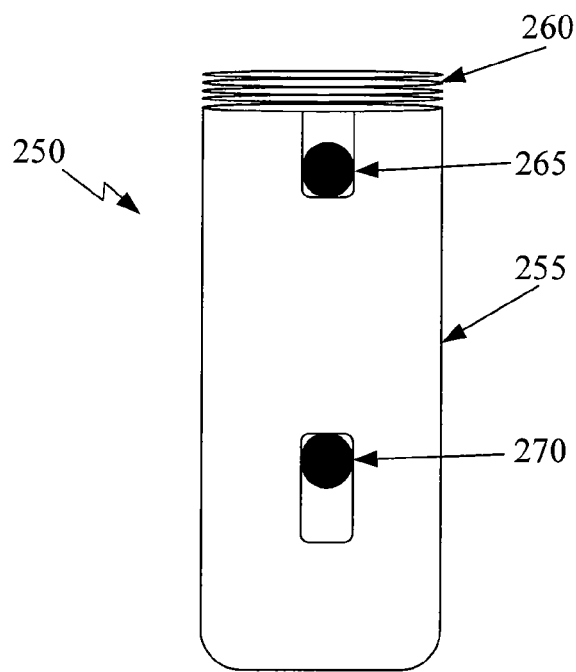
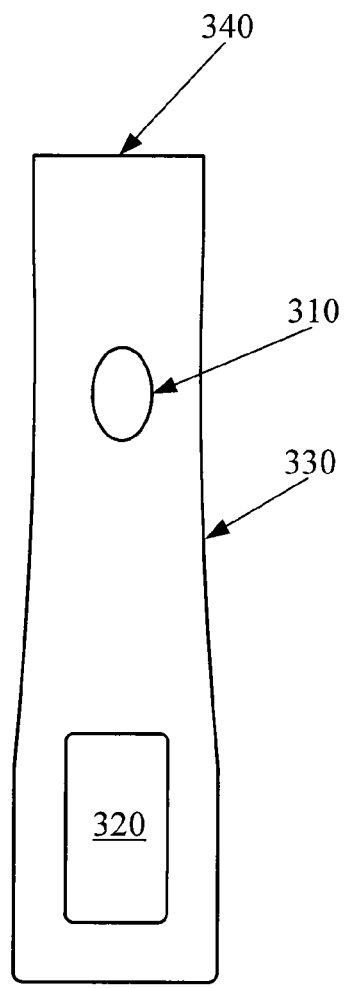
Fig. 2
Fig. 3

TEMPERATURE CONTROL DEVICE AND THERMAL SENSOR ASSEMBLY FOR MEDICAL DEVICE

RELATED APPLICATIONS

This Application is a continuation-in-part of U.S. patent application Ser. No. 11/581,629 filed Oct. 16, 2006, U.S. patent application Ser. No. 11/581,630 filed Oct. 16, 2006, U.S. patent application Ser. No. 11/581,591 filed Oct. 16, 2006, and is related to U.S. patent application Ser. No. 11/435,906 filed May 17, 2006.

BACKGROUND OF THE INVENTION

The present invention relates to a single-use medical device and more particularly to a two-piece ophthalmic injection device with a disposable tip end containing a temperature control device and temperature sensor assembly.

Several diseases and conditions of the posterior segment of the eye threaten vision. Age related macular degeneration (ARMD), choroidal neovascularization (CNV), retinopathies (e.g., diabetic retinopathy, vitreoretinopathy), retinitis (e.g., cytomegalovirus (CMV) retinitis), uveitis, macular edema, glaucoma, and neuropathies are several examples.

These, and other diseases, can be treated by injecting a drug into the eye. Such injections are typically manually performed using a conventional syringe and needle. FIG. 1 is a perspective view of a prior art syringe used to inject drugs into the eye. In FIG. 1, the syringe includes a needle 105, a luer hub 110, a chamber 115, a plunger 120, a plunger shaft 125, and a thumb rest 130. As is commonly known, the drug to be injected is located in chamber 115. Pushing on the thumb rest 130 causes the plunger 120 to expel the drug through needle 105.

In using such a syringe, the surgeon is required to pierce the eye tissue with the needle, hold the syringe steady, and actuate the syringe plunger (with or without the help of a nurse) to inject the fluid into the eye. The volume injected is typically not controlled in an accurate manner because reading the vernier is subject to parallax error. Fluid flow rates are uncontrolled. and tissue damage may occur due to an "unsteady" injection. Reflux of the drug may also occur when the needle is removed from the eye.

An effort has been made to control the delivery of small amounts of liquids. A commercially available fluid dispenser is the ULTRA™ positive displacement dispenser available from EFD Inc. of Providence, R.I. The ULTRA dispenser is typically used in the dispensing of small volumes of industrial adhesives. It utilizes a conventional syringe and a custom dispensing tip. The syringe plunger is actuated using an electrical stepper motor and an actuating fluid. With this type of dispenser, the volumes delivered are highly dependent on fluid viscosity, surface tension, and the specific dispensing tip. Parker Hannifin Corporation of Cleveland, Ohio distributes a small volume liquid dispenser for drug discovery applications made by Aurora Instruments LLC of San Diego, Calif. The Parker/Aurora dispenser utilizes a piezo-electric dispensing mechanism. While precise, this dispenser is expensive and requires an electrical signal to be delivered to the dispensing mechanism.

U.S. Pat. No. 6,290,690 discloses an ophthalmic system for injecting a viscous fluid (e.g. silicone oil) into the eye while simultaneously aspirating a second viscous fluid (e.g. perfluorocarbon liquid) from the eye in a fluid/fluid exchange during surgery to repair a retinal detachment or tear. The system includes a conventional syringe with a plunger. One end of the syringe is fluidly coupled to a source of pneumatic pressure that provides a constant pneumatic pressure to actuate the plunger. The other end of the syringe is fluidly coupled to an infusion cannula via tubing to deliver the viscous fluid to be injected.

It would be desirable to have a portable hand piece for injecting a drug into the eye. Such a hand piece can include a limited reuse assembly attachable to and removable from a disposable tip segment. The disposable tip segment contains the drug, a needle for administering the drug, and a temperature control device, such as a heater, for altering the temperature of the drug. In order to facilitate assembly of the device, it would be desirable to have a temperature control device integrated with a thermal sensor in a single assembly.

SUMMARY OF THE INVENTION

In one embodiment consistent with the principles of the present invention, the present invention is a dispensing assembly with a dispensing chamber housing, a temperature control device, and a thermal sensor. The dispensing chamber housing has an inner surface, an outer surface, and a wall thickness. The inner surface partially defines a dispensing chamber for receiving a quantity of a substance. The temperature control device at least partially surrounds the dispensing chamber housing. The temperature control device alters a temperature of a substance in the dispensing chamber. The temperature control device and the thermal sensor are located on the substrate.

In another embodiment consistent with the principles of the present invention, the present invention is a single piece temperature control assembly. The assembly includes a temperature control device and a thermal sensor located on a substrate. The thermal sensor is arranged on the substrate such that the distance between the thermal sensor and the temperature control device is approximately equal to the distance between the temperature control device and a substance whose temperature is to be altered by the temperature control device.

In another embodiment consistent with the principles of the present invention, the present invention is a dispensing assembly having a dispensing chamber housing, a temperature control device, a thermal sensor, and an interface. The dispensing chamber housing has an inner surface, an outer surface, and a wall thickness. The inner surface partially defines a dispensing chamber for receiving a quantity of a substance. The temperature control device at least partially surrounds the dispensing chamber housing. The temperature control device alters a temperature of a substance in the dispensing chamber. The temperature control device and the thermal sensor are located on a substrate. The interface is connected to the temperature control device and the thermal sensor. An interface connector is connected to the interface. The distance between the temperature control device and the thermal sensor is approximately equal to the wall thickness of the dispensing chamber housing. The substrate is wrapped around an exterior surface of the dispensing chamber housing.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying figures, which are incorporated in and constitute a part of this specification, illustrate several embodiments of the invention and together with the description, serve to explain the principles of the invention.

FIG. 2 is a view of an ophthalmic medical device including a disposable tip segment and a limited reuse assembly according to the principles of the present invention.

FIG. 3 is an embodiment of a limited reuse assembly according to the principles of the present invention.

DETAILED DESCRIPTION OF THE PREFERRED EMBODIMENTS

Figure 1:
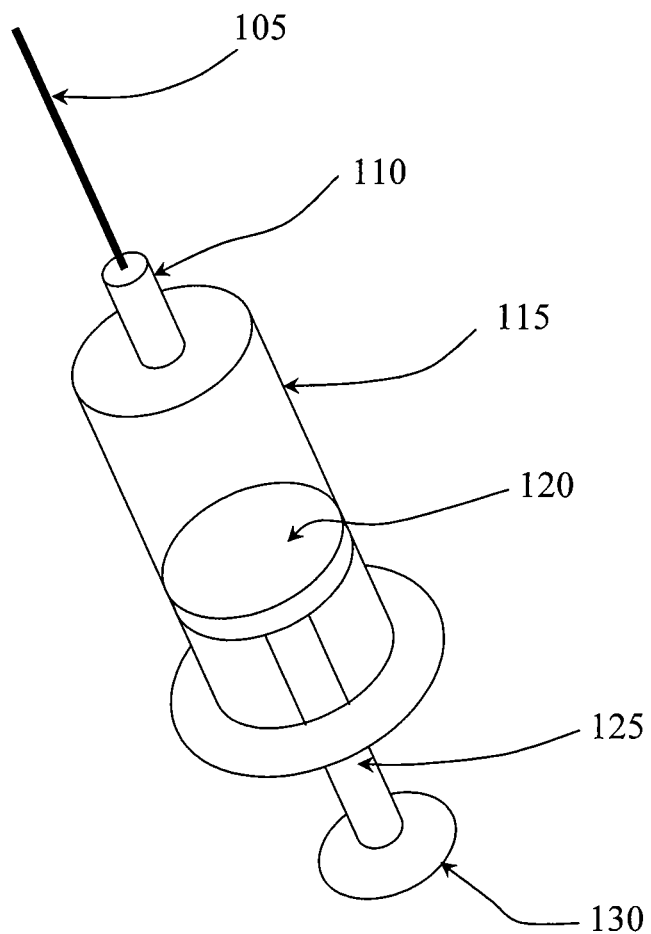
FIG. 1 is a perspective view of a prior art syringe.

Reference is now made in detail to the exemplary embodiments of the invention, examples of which are illustrated in the accompanying figures. Wherever possible, the same reference numbers are used throughout the figures to refer to the same or like parts.

FIG. 2 depicts one view of an ophthalmic medical device including a disposable tip segment and a limited reuse assembly according to an embodiment of the present invention. In FIG. 2, the medical device includes a tip segment 205 and a limited reuse assembly 250. The tip segment 205 includes a needle 210, a housing 215, and an optional light 275. The limited reuse assembly 250 includes a housing 255, a switch 270, a lock mechanism 265, and a threaded portion 260.

Tip segment 205 is capable of being connected to and removed from limited reuse assembly 250. In this embodiment, tip segment 205 has a threaded portion on an interior surface of housing 215 that screws onto the threaded portion 260 of limited reuse assembly 250. In addition, lock mechanism 265 secures tip segment 215 to limited reuse assembly 250. Lock mechanism 265 may be in the form of a button, a sliding switch, or a cantilevered mechanism. Other mechanisms for connecting tip segment 205 to limited reuse assembly 250, such as those involving structural features that mate with each other, are commonly known in the art and are within the scope of the present invention.

Needle 210 is adapted to deliver a substance, such as a drug, into an eye. Needle 210 may be of any commonly known configuration. Preferably, needle 210 is designed such that its thermal characteristics are conducive to the particular drug delivery application. For example, when a heated drug is to be delivered, needle 210 may be relatively short (several millimeters) in length to facilitate proper delivery of the drug based on thermal characteristics.

Switch 270 is adapted to provide an input to the system. For example, switch 270 may be used to activate the system or to turn on a heater. Other switches, buttons, or user-directed control inputs are commonly known and may be employed with limited reuse assembly 250 and/or tip segment 205.

Optional light 275 is illuminated when tip segment 205 is ready to be used. Optional light 275 may protrude from housing 215, or it may be contained within housing 215, in which case, optional light 275 may be seen through a clear portion of housing 215. In other embodiments, optional light 275 may be replaced by an indicator, such as a liquid crystal display, segmented display, or other device that indicates a status or condition of disposable tip segment 205. For example, optional light 275 may also pulse on and off to indicate other states, such as, but not limited to a system error, fully charged battery, insufficiently charged battery or faulty connection between the tip segment 205 and limited use assembly 250. While shown on tip segment 205, optional light 275 or another indicator may be located on limited reuse assembly 250.

FIG. 3 is another embodiment of a limited reuse assembly according to the principles of the present invention. Limited reuse assembly 250 includes a button 310, a display 320, and a housing 330. Disposable tip segment 205 attaches to end 340 of limited reuse assembly 250. Button 310 is actuated to provide an input to the system. As with switch 270, button 310 may activate a heater or other temperature control device or initiate actuation of a plunger. Display 320 is a liquid crystal display, segmented display, or other device that indicates a status or condition of disposable tip segment 205 or limited reuse assembly 250.

Figure 4:
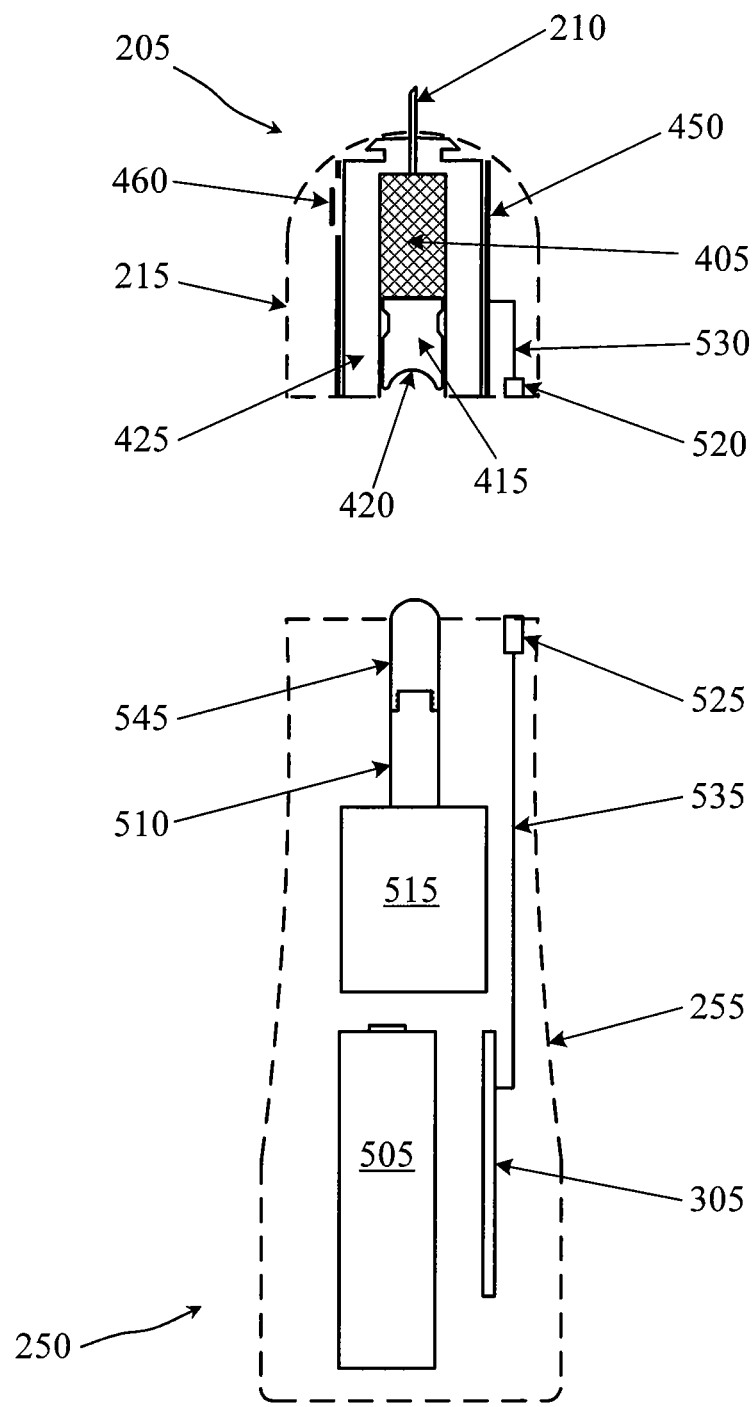
FIG. 4 is a cross section view of a disposable tip segment and a limited reuse assembly according to the principles of the present invention.

FIG. 4 is a cross section view of a disposable tip segment and a limited reuse assembly according to an embodiment of the present invention. FIG. 4 shows how tip segment 205 interfaces with limited reuse assembly 250. In the embodiment of FIG. 4, tip segment 205 includes plunger interface 420, plunger 415, dispensing chamber housing 425, tip segment housing 215, temperature control device 450, thermal sensor 460, needle 210, dispensing chamber 405, interface 530, and tip interface connector 520. Limited reuse assembly 250 includes mechanical linkage 545, actuator shaft 510, actuator 515, power source 505, controller 305, limited reuse assembly housing 255, interface 535, and limited reuse assembly interface connector 525.

In tip segment 205, plunger interface 420 is located on one end of plunger 415. The other end of plunger 415 forms one end of dispensing chamber 405. Plunger 415 is adapted to slide within dispensing chamber 405. An outer surface of plunger 415 is fluidly sealed to the inner surface of dispensing chamber housing 425. Dispensing chamber housing 425 surrounds the dispensing chamber 405. Typically, dispensing chamber housing 425 has a cylindrical shape. As such, dispensing chamber 405 also has a cylindrical shape.

Needle 210 is fluidly coupled to dispensing chamber 405. In such a case, a substance contained in dispensing chamber 405 can pass through needle 210 and into an eye. Temperature control device 450 at least partially surrounds dispensing chamber housing 425. In this case, temperature control device 450 is adapted to heat and/or cool dispensing chamber housing 425 and any substance contained in dispensing chamber 405. The arrangement of temperature control device 450 and dispensing thermal sensor 460 is described in more detail below. Interface 530 connects temperature control device 450 and thermal sensor 460 with tip interface connector 520.

The components of tip segment 205, including dispensing chamber housing 425, temperature control device 450, and plunger 415 are at least partially enclosed by tip segment housing 215. In one embodiment consistent with the principles of the present invention, plunger 415 is sealed to the interior surface of dispensing chamber housing 425. This seal prevents contamination of any substance contained in dispensing chamber 405. For medical purposes, such a seal is desirable. This seal can be located at any point on plunger 415 or dispensing chamber housing 425.

In limited reuse assembly 250, power source 505 provides power to actuator 515. An interface (not shown) between power source 505 and actuator 515 serves as a conduit for providing power to actuator 515. Actuator 515 is connected to actuator shaft 510. When actuator 515 is a stepper motor, actuator shaft 510 is integral with actuator 515. Mechanical linkage interface 545 is connected to actuator shaft 510. In this configuration, as actuator 515 moves actuator shaft 510 upward toward needle 210 mechanical linkage interface 545 also moves upward toward needle 210.

Controller 305 is connected via interface 535 to limited reuse assembly interface connector 525. Limited reuse assembly interface connector 525 is located on a top surface of limited reuse assembly housing 255 adjacent to mechanical linkage interface 545. In this manner, both limited reuse assembly interface connector 525 and mechanical linkage interface 545 are adapted to be connected with tip interface connector 520 and plunger interface 420 respectively.

Controller 305 and actuator 515 are connected by an interface (not shown). This interface (not shown) allows controller 305 to control the operation of actuator 515. In addition, an interface (not shown) between power source 505 and controller 305 allows controller 305 to control operation of power source of 310. In such a case, controller 305 may control the charging and the discharging of power source 505 when power source 505 is a rechargeable battery.

Controller 305 is typically an integrated circuit with power, input, and output pins capable of performing logic functions. In various embodiments, controller 305 is a targeted device controller. In such a case, controller 305 performs specific control functions targeted to a specific device or component, such as a temperature control device or a power supply. For example, a temperature control device controller has the basic functionality to control a temperature control device. In other embodiments, controller 305 is a microprocessor. In such a case, controller 305 is programmable so that it can function to control more than one component of the device. In other cases, controller 305 is not a programmable microprocessor, but instead is a special purpose controller configured to control different components that perform different functions. While depicted as one component, controller 305 may be made of many different components or integrated circuits.

Figure 5:
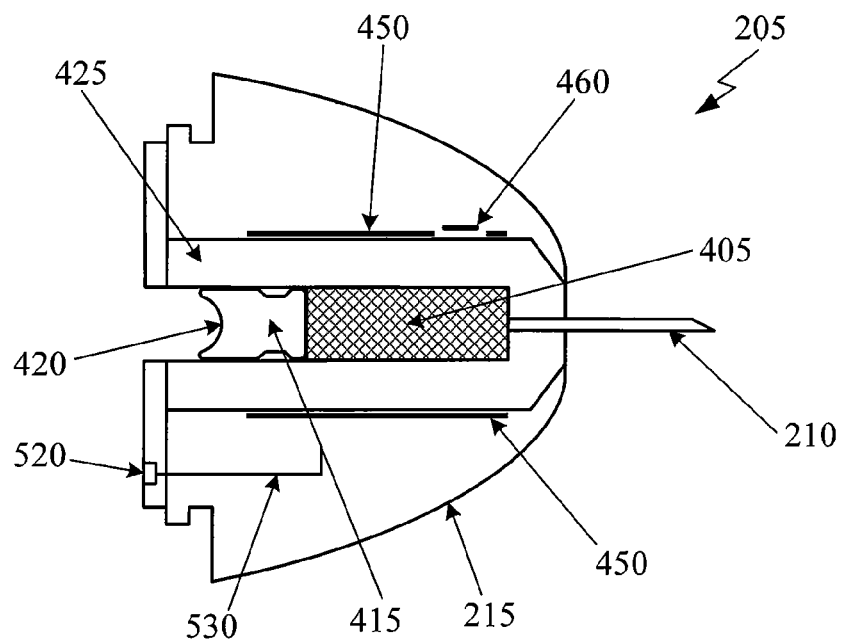
FIG. 5 is a cross section view of a disposable tip segment according to the principles of the present invention.

Tip segment 205 is adapted to mate with or attach to limited reuse assembly 250 as previously described. In the embodiment of FIG. 5, plunger interface 420 located on a bottom surface of plunger 415 is adapted to mate with mechanical linkage interface 545 located near a top surface of limited reuse assembly housing 255. In addition, tip interface connector 520 is adapted to connect with limited reuse assembly interface connector 525. When tip segment 205 is connected to limited reuse assembly 250 in this manner, actuator 515 and actuator shaft 510 are adapted to drive plunger 415 upward toward needle 210. In addition, an interface is formed between controller 305 and temperature control device 450. A signal can pass from controller 305 to temperature control device 450 through interface 535, limited reuse assembly interface connector 525, tip interface connector 520, and interface 530.

In operation, when tip segment 205 is connected to limited reuse assembly 250, controller 305 controls the operation of actuator 515. Actuator 515 is actuated and actuator shaft 510 is moved upward toward needle 210. In turn, mechanical linkage interface 545, which is mated with plunger interface 420, moves plunger 415 upward toward needle 210. A substance located in dispensing chamber 405 is then expelled through needle 210.

In addition, controller 305 controls the operation of temperature control device 450. Temperature control device 450 is adapted to heat and/or cool dispensing chamber housing 425. Since dispensing chamber housing 425 is at least partially thermally conductive, heating or cooling dispensing chamber housing 425 heats or cools a substance located in dispensing chamber 405. Temperature information can be transferred from thermal sensor 460 to controller 305 via any of a number of different interface configurations. This temperature information can be used to control the operation of temperature control device 450. When temperature control device 450 is a heater, controller 305 controls the amount of current that is sent to temperature control device 450. The more current sent to temperature control device 450, the hotter it gets. In such a manner, controller 305 can use a feed back loop utilizing information from thermal sensor 460 to control the operation of temperature control device 450. Any suitable type of control algorithm, such as a proportional integral derivative (PID) algorithm, can be used to control the operation of temperature control device 450.

FIG. 5 is a cross section view of a disposable tip segment for an ophthalmic medical device according to an embodiment of the present invention. In FIG. 5, disposable tip segment 205 includes housing 215, needle 210, plunger 415, plunger interface 420, dispensing chamber 405, dispensing chamber housing 425, temperature control device 450, thermal sensor 460, interface 530, and tip interface connector 520. Disposable tip segment 205 operates as a disposable injection device.

In the embodiment of FIG. 5, plunger 415 is located in dispensing chamber housing 425. Dispensing chamber 405 is enclosed by dispensing chamber housing 425 and plunger 415. Plunger 415 forms a fluid seal with the interior surface of dispensing chamber housing 425. Needle 210 is fluidly coupled to dispensing chamber 405. In this manner, a substance located in dispensing chamber 405 can be contacted by plunger 415 and pushed out of needle 210. Temperature control device 450 is located adjacent to dispensing chamber housing 425 and at least partially surrounds dispensing chamber 405. Housing 215 forms an outer skin on disposable tip segment 205.

In various embodiments of the present invention, temperature control device 450 is a heating and/or a cooling device. Temperature control device 450 is in thermal contact with dispensing chamber housing 425. As such, temperature control device 450 is capable of changing the temperature of the substance in dispensing chamber 405. Interface 530 and tip interface connector 520 couple temperature control device 450 to a limited reuse assembly. In such a case, temperature control device 450 can be powered and controlled by the limited reuse assembly. In one embodiment of the present invention, temperature control device 450 receives current via interface 530 from a limited reuse assembly. Providing current in one direction (i.e., a positive voltage across the device) causes temperature control device 450 to heat. Providing current in the opposite direction (i.e., a negative voltage across the device) causes temperature control device 450 to cool.

A substance to be delivered into an eye, typically a drug, is located in dispensing chamber 405. In this manner, the substance is contacted by the inner surface of dispensing chamber housing 425 and one face of plunger 415. Typically, dispensing chamber 405 is cylindrical in shape. Temperature control device 450 is in thermal contact with dispensing chamber housing 425. In this manner, temperature control device 450 is adapted to control the temperature of the contents of dispensing chamber 425. Thermal sensor 460 provides temperature information to assist in controlling the operation of temperature control device 450.

In one embodiment of the present invention, the substance located in dispensing chamber 405 is a drug that is preloaded into the dispensing chamber. In such a case, disposable tip segment 205 is appropriate as a single use consumable product. Such a disposable product can be assembled at a factory with a dosage of a drug installed.

When a drug is preloaded into dispensing chamber 405, a set quantity of the drug can be preloaded. For example, 100 microliters of a drug can be loaded into dispensing chamber 405, and any quantity up to 100 microliters can be dispensed. In such a case, the plunger 415 can be moved a precise distance to deliver a precise dosage of drug from the dispensing chamber 405, through the needle 210, and into an eye. This provides for flexibility of dosing and for ease of assembly.

Figure 6A:
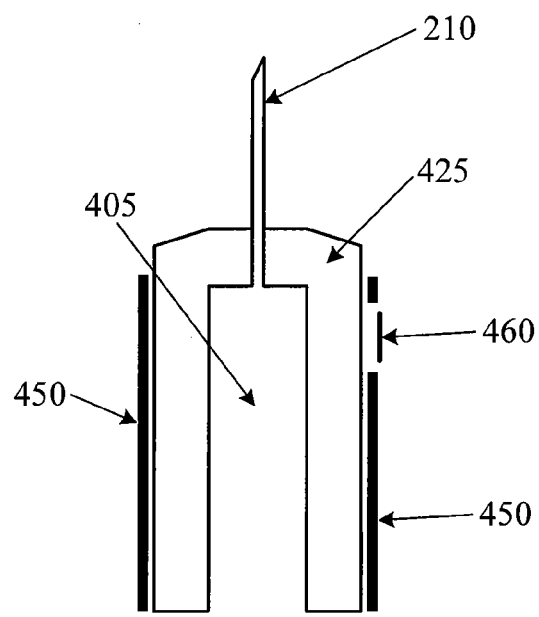
FIGS. 6A and 6B are cross section views of a dispensing chamber housing assembly according to the principles of the present invention.

FIG. 6A is a cross section view of a dispensing chamber housing assembly according to the principles of the present invention. In FIG. 6, dispensing chamber housing 425 is generally cylindrical in shape. Dispensing chamber 405 is located inside a cavity at least partially defined by the interior surface of dispensing chamber housing 425. Temperature control device 450 at least partially surrounds dispensing chamber housing 425. Temperature control device 450 and thermal sensor 460 are integrated into a single assembly that is wrapped around the exterior surface of dispensing chamber housing 425. In one embodiment of the present invention, thermal sensor 460 is a thermistor.

Figure 6B:
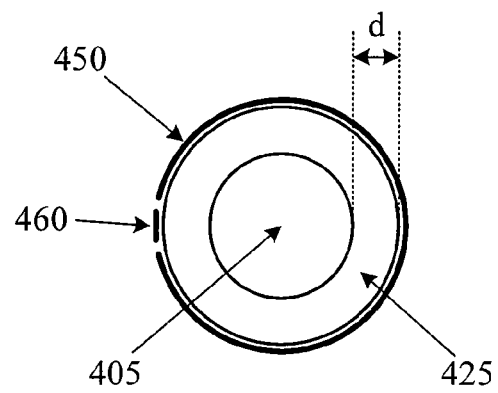

FIG. 6B is a cross section view of a dispensing chamber housing assembly according to the principles of the present invention. This view is a horizontal cross section of the embodiment of FIG. 6A (which is a vertical cross section). In FIG. 6B, dispensing chamber housing has a generally circular cross section (because it is generally cylindrical in shape). The wall thickness of dispensing chamber housing is "d." Dispensing chamber 405 is located inside dispensing chamber housing 425. Temperature control device 450 at least partially surrounds dispensing chamber housing 425. Thermal sensor 460 is located adjacent to dispensing chamber housing 425.

Figure 7A:
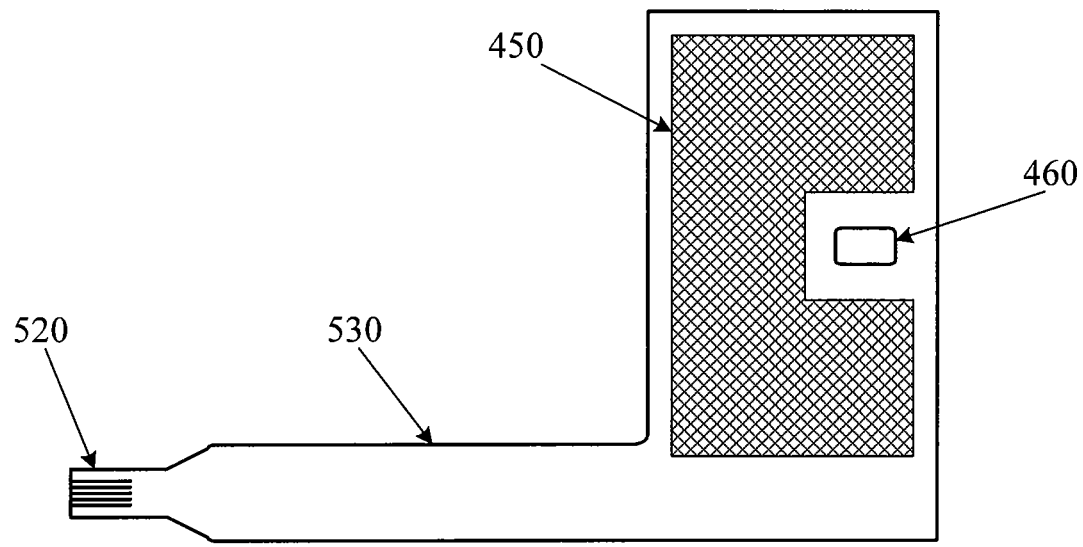
FIGS. 7A & 7B are views of a temperature control device and thermal sensor assembly according to the principles of the present invention.

FIG. 7A depicts a temperature control device and thermal sensor assembly according to an embodiment of the present invention. In FIG. 7A, temperature control device 450 is arranged on a substrate (for example, a flexible printed circuit board or similar structure) as shown. In its simplest form, temperature control device is a resistive element that produces heat when a current is passed through it. Thermal sensor 460 is located on the same substrate as temperature control device 450. Interface 530 and tip interface connector 520 serve to link temperature control device 450 and thermal sensor 460 to a limited reuse assembly.

Figure 7B:
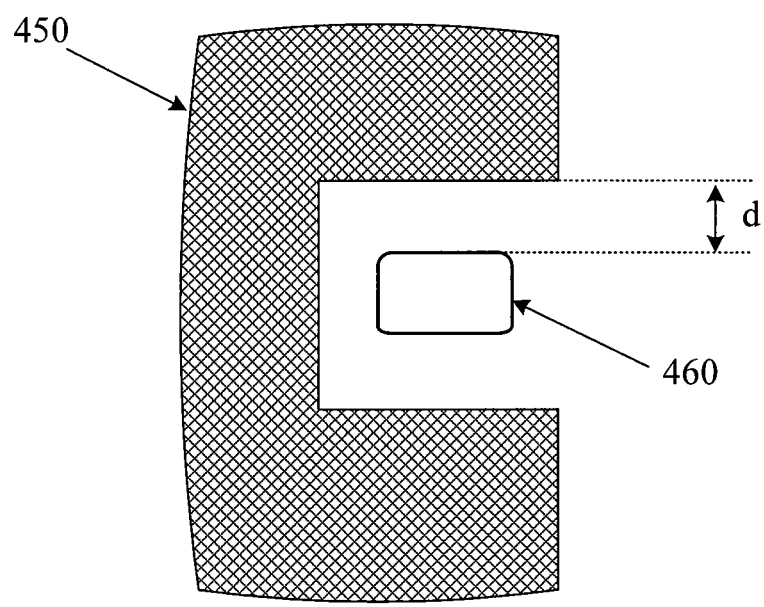

FIG. 7B is a larger view of a portion of the temperature control device and the thermal sensor of FIG. 7A. In FIG. 7B, the arrangement of thermal sensor 460 and temperature control device 450 is shown. Thermal sensor 460 is located a distance "d" from temperature control device 450. This distance "d" is approximately equal to the thickness of the dispensing chamber housing 425 as shown in FIG. 6B. In this manner, thermal sensor 460 reads a temperature that is approximately equal to the temperature on the interior of dispensing chamber housing 425. Since the distance "d" is the distance between the temperature control device 450 and both the thermal sensor 460 and the dispensing chamber 405, thermal sensor 460 is located such that it reads a temperature that approximates the temperature in dispensing chamber 405.

From the above, it may be appreciated that the present invention provides an improved system for delivering precise volumes of a substance into an eye. The present invention provides a single use, disposable delivery device tip segment that is capable of delivering a dosage of a drug. The tip segment interfaces with a limited reuse assembly. The disposable tip segment has an assembly that includes a temperature control device and a thermal sensor. The construction of the assembly allows for easy manufacture and assembly of the device while allowing for reliable injection procedures.

While the present invention is described in the context of a single-use ophthalmic drug delivery device, the present invention encompasses any medical device or injection device. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A dispensing assembly comprising:
   a dispensing chamber housing having an inner surface, an outer surface, and a wall thickness; the inner surface partially defining a dispensing chamber for receiving a quantity of a substance;
   an electrical temperature control device located on a flexible substrate and at least partially surrounding the dispensing chamber housing, the electrical temperature control device covering a first area comprising most of a surface area of the substrate, the temperature control device for altering a temperature of a substance in the dispensing chamber; and
   a thermal sensor located on a second area of the substrate the second area smaller than the first area;
   wherein a distance between the electrical temperature control device and the thermal sensor on the second area of the substrate is approximately equal to the wall thickness of the dispensing chamber housing.

2. The assembly of claim 1 wherein the dispensing chamber housing is generally cylindrical in shape.

3. The assembly of claim 1 further comprising:
   an interface connected to the temperature control device and the thermal sensor; and
   an interface connector connected to the interface.

4. The assembly of claim 3 wherein power is provided to the temperature control device through the interface.

5. The assembly of claim 3 wherein temperature information passes from the thermal sensor through the interface.

6. The assembly of claim 1 wherein the thermal sensor is a thermistor.

7. The assembly of claim 1 wherein the temperature control device is a heater comprising a resistive element.

8. The assembly of claim 1 further comprising:
   a needle fluidly coupled to the dispensing chamber.

9. The assembly of claim 1 wherein the substrate is wrapped around an exterior surface of the dispensing chamber housing.

10. A single piece temperature control assembly comprising:
- a flexible substrate;
- an electrical temperature control device located on the substrate, the electrical temperature control device covering a first area comprising most of a surface area of the substrate;
- a thermal sensor arranged on a second area of the substrate such that a distance between the thermal sensor and the electrical temperature control device on the substrate is approximately equal to a distance between the temperature control device and a substance whose temperature is to be altered by the temperature control device.

11. The assembly of claim 10 further comprising:
- an interface connected to the temperature control device and the thermal sensor; and
- an interface connector connected to the interface.

12. The assembly of claim 10 wherein the thermal sensor is a thermistor.

13. The assembly of claim 10 wherein the temperature control device is a heater comprising a resistive element.

14. A dispensing assembly comprising:
- a dispensing chamber housing having an inner surface and an outer surface, the inner surface partially defining a dispensing chamber for receiving a quantity of a substance, the dispensing chamber housing having a wall thickness;
- an electrical temperature control device located on a substrate and at least partially surrounding the dispensing chamber housing, the electrical temperature control device covering a first area comprising most of a surface area of the substrate, the temperature control device for altering a temperature of a substance in the dispensing chamber;
- a thermal sensor located on a second area of the substrate;
- an interface connected to the temperature control device and the thermal sensor; and
- an interface connector connected to the interface;
- wherein a distance between the electrical temperature control device and the thermal sensor on the substrate is approximately equal to the wall thickness of the dispensing chamber housing and wherein the substrate is wrapped around an exterior surface of the dispensing chamber housing.

15. The assembly of claim 14 wherein the dispensing chamber housing is generally cylindrical in shape.

16. The assembly of claim 14 wherein power is provided to the temperature control device through the interface.

17. The assembly of claim 14 wherein temperature information passes from the thermal sensor through the interface.

18. The assembly of claim 14 wherein the thermal sensor is a thermistor.

19. The assembly of claim 14 wherein the temperature control device is a heater comprising a resistive element.

* * * * *